(12) United States Patent
Hartwell et al.

(10) Patent No.: US 8,333,744 B2
(45) Date of Patent: Dec. 18, 2012

(54) APPARATUS FOR THE PROVISION OF TOPICAL NEGATIVE PRESSURE THERAPY

(76) Inventors: Edward Hartwell, York (GB); Carl Saxby, York (GB)

( * ) Notice: Subject to any disclaimer, the term of this patent is extended or adjusted under 35 U.S.C. 154(b) by 372 days.

(21) Appl. No.: 12/672,192

(22) PCT Filed: Jul. 18, 2008

(86) PCT No.: PCT/GB2008/050591
§ 371 (c)(1),
(2), (4) Date: Feb. 4, 2010

(87) PCT Pub. No.: WO2009/019501
PCT Pub. Date: Feb. 12, 2009

(65) Prior Publication Data
US 2011/0130730 A1    Jun. 2, 2011

(30) Foreign Application Priority Data
Aug. 6, 2007 (GB) .................................. 0715212.7

(51) Int. Cl.
*A61M 1/00* (2006.01)
(52) U.S. Cl. ........ 604/319; 604/187; 604/192; 604/268; 604/289; 604/290; 604/296; 604/300; 604/304; 604/305; 604/311; 604/312; 604/313; 604/315; 604/316; 604/318; 604/35; 604/36; 604/119
(58) Field of Classification Search .................. 604/315, 604/316, 318, 319
See application file for complete search history.

(56) References Cited

U.S. PATENT DOCUMENTS

| 4,969,880 | A | 11/1990 | Zamierowski |
| 5,096,385 | A | 3/1992 | Georgi et al. |
| 5,527,293 | A | 6/1996 | Zamierowski |
| 5,636,643 | A | 6/1997 | Argenta et al. |
| 5,645,081 | A | 7/1997 | Argenta et al. |
| 5,738,656 | A | 4/1998 | Wagner |
| 6,071,267 | A | 6/2000 | Zamierowski |
| 6,117,111 | A | 9/2000 | Fleischmann |
| 6,142,982 | A | 11/2000 | Hunt et al. |
| 6,345,623 | B1 | 2/2002 | Heaton et al. |
| 6,648,862 | B2 | 11/2003 | Watson et al. |
| 6,685,681 | B2 | 2/2004 | Lockwood et al. |
| 6,752,794 | B2 | 6/2004 | Lockwood et al. |

(Continued)

FOREIGN PATENT DOCUMENTS
EP          0394687 A     10/1990
(Continued)

OTHER PUBLICATIONS
Info V.A.C. User Manual—KCI—Dec. 2006 (76 pages).
(Continued)

*Primary Examiner* — Tatyana Zalukaeva
*Assistant Examiner* — Ilya Treyger
(74) *Attorney, Agent, or Firm* — Knobbe, Martens, Olson & Bear LLP

(57) ABSTRACT

Apparatus for the provision of topical negative pressure therapy to a user is described, the apparatus comprising a device and a waste canister connected thereto, the waste canister being operably connected for receiving wound exudate to a wound dressing by an aspiration conduit which is releasably connected to the dressing, wherein the waste canister has a blank connector portion thereon for sealably receiving a disconnected dressing end of the aspiration conduit.

19 Claims, 10 Drawing Sheets

U.S. PATENT DOCUMENTS

| | | | |
|---|---|---|---|
| 6,824,533 B2 * | 11/2004 | Risk, Jr. et al. | 604/319 |
| 6,936,037 B2 | 8/2005 | Bubb et al. | |
| 7,004,915 B2 | 2/2006 | Boynton et al. | |
| 7,022,113 B2 | 4/2006 | Lockwood et al. | |
| 7,108,683 B2 | 9/2006 | Zamierowski | |
| 7,195,624 B2 | 3/2007 | Lockwood et al. | |
| 7,198,046 B1 | 4/2007 | Argenta et al. | |
| 7,216,651 B2 | 5/2007 | Argenta et al. | |
| 7,381,859 B2 | 6/2008 | Hunt et al. | |
| 7,438,705 B2 * | 10/2008 | Karpowicz et al. | 604/313 |
| D587,901 S | 3/2009 | Pidgeon et al. | |
| 7,503,910 B2 | 3/2009 | Adahan | |
| 7,534,927 B2 | 5/2009 | Lockwood et al. | |
| 7,553,306 B1 | 6/2009 | Hunt et al. | |
| D602,582 S | 10/2009 | Pidgeon et al. | |
| D602,583 S | 10/2009 | Pidgeon et al. | |
| D602,584 S | 10/2009 | Pidgeon et al. | |
| 7,604,610 B2 | 10/2009 | Shener et al. | |
| 7,611,500 B1 | 11/2009 | Lina et al. | |
| 7,625,362 B2 | 12/2009 | Boehringer et al. | |
| D607,202 S | 1/2010 | Pidgeon et al. | |
| 7,670,323 B2 | 3/2010 | Hunt et al. | |
| D617,094 S | 6/2010 | Pidgeon et al. | |
| 7,759,538 B2 | 7/2010 | Fleischmann | |
| D625,801 S | 10/2010 | Pidgeon et al. | |
| D630,313 S | 1/2011 | Pidgeon et al. | |
| D630,725 S | 1/2011 | Pidgeon et al. | |
| D645,137 S | 9/2011 | Gonzalez | |
| D650,894 S | 12/2011 | Gonzalez | |
| 8,070,735 B2 | 12/2011 | Koch et al. | |
| 2008/0125698 A1 | 5/2008 | Gerg et al. | |
| 2009/0163882 A1 | 6/2009 | Koch et al. | |
| 2009/0306580 A1 | 12/2009 | Blott et al. | |
| 2010/0063464 A1 | 3/2010 | Meyer et al. | |
| 2010/0094234 A1 | 4/2010 | Ramella et al. | |
| 2010/0100075 A1 | 4/2010 | Weston et al. | |
| 2010/0185164 A1 | 7/2010 | Hartwell et al. | |
| 2010/0185165 A1 | 7/2010 | Middleton et al. | |
| 2010/0187065 A1 | 7/2010 | Pidgeon et al. | |
| 2010/0207768 A1 | 8/2010 | Pidgeon et al. | |
| 2010/0244780 A1 | 9/2010 | Turner et al. | |
| 2010/0298792 A1 | 11/2010 | Weston et al. | |
| 2011/0008179 A1 | 1/2011 | Turner et al. | |
| 2011/0054810 A1 | 3/2011 | Turner et al. | |
| 2012/0001762 A1 | 1/2012 | Turner et al. | |

FOREIGN PATENT DOCUMENTS

| | | |
|---|---|---|
| EP | 0688189 B2 | 12/1995 |
| EP | 0777504 B1 | 10/1998 |
| EP | 0853950 B1 | 10/2002 |
| EP | 1219311 B1 | 7/2004 |
| EP | 1440667 B1 | 7/2004 |
| EP | 1171065 B1 | 3/2007 |
| EP | 1121163 B1 | 11/2008 |
| GB | 1 334 840 | 10/1973 |
| WO | WO 97/26928 A | 7/1997 |
| WO | WO 98/48953 A | 11/1998 |
| WO | WO 03/101508 | 12/2003 |
| WO | WO 2006/052745 | 5/2006 |
| WO | WO 2006/105892 | 10/2006 |
| WO | WO 2006/114638 | 11/2006 |
| WO | WO 2006/135934 | 12/2006 |
| WO | WO 2007/013064 | 2/2007 |
| WO | WO 2008/010094 | 1/2008 |
| WO | WO 2008/030872 | 3/2008 |
| WO | WO 2008/036360 | 3/2008 |
| WO | WO 2008/039314 | 4/2008 |
| WO | WO 2008/048527 | 4/2008 |

OTHER PUBLICATIONS

International Search Report from PCT/GB2008/050591, dated Jan. 15, 2009 in 5 pages.

Written Opinion of the International Searching Authority from PCT/GB2008/050591, dated Jan. 15, 2009 in 6 pages.

Zivadinovic, Gorica, Veljko Dukic, Zivan Maksimovic, Dorde Radak and Predrag Pesko, Vacuum Therapy in the Treatment of Peripheral Blood Vessels, Timocki . Medicinski Glasnik (Conference Papers of the 5th Timok Medical Days, Majdanepek, 1986), Year XI, Zajecar, 1986, No. 3-4, pp. 161-164 (with English translation).

* cited by examiner

APPARATUS FOR THE PROVISION OF TOPICAL NEGATIVE PRESSURE THERAPY

CROSS-REFERENCE TO RELATED APPLICATIONS

This Application is a U.S. National Phase of the International Application No. PCT/GB2008/050591 filed Jul. 18, 2008 designating the U.S. and published on Feb. 12, 2009 as WO 2009/019501, which claims priority of Great Britain Patent Application No. 0715212.7 filed Aug. 6, 2007.

BACKGROUND OF THE INVENTION

1. Field of the Invention

The present invention relates to apparatus and a method for the application of topical negative pressure (TNP) therapy to wounds. In particular, but not exclusively, the present invention relates to management of waste fluid when changing or disconnecting a waste fluid canister of a TNP therapy apparatus.

2. Background of the Invention

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

GB-A-2 307 180 describes a portable TNP therapy unit which may be carried by a patient clipped to a belt or harness. When the waste canister of the apparatus is full or otherwise needs changing, the aspiration tube needs to be disconnected form the wound dressing, however, there appears to be no provision for preventing possible leakage of wound exudate from the aspiration tube other than by the use of a separate clamp on the tube. The use of a separate clamp is inconvenient and such a clamp may be forgotten by the user. Such separate clamps are known to be awkward and cumbersome and furthermore provide a risk to the user if lain upon by the formation of pressure ulcers. Once clamped the aspiration tube may continue to drip as it is not possible to clamp the very end of the tube and such dripping may pose a risk of infection to both the user and others.

Additionally, some countries have legislation concerning the disposal of biohazard material in that the container must maintain integrity up to a specified pressure. Tube clamps are known to be unreliable and prone to inadvertent release or improper operation.

SUMMARY OF SOME EXEMPLIFYING EMBODIMENTS

It is an aim of the present invention to at least partly mitigate the above-mentioned problems.

It is an aim of embodiments of the present invention to provide a means of sealing a waste canister against leakage of wound exudate when the aspiration conduit is disconnected therefrom without the need for the user to carry a separate clamping device to squeeze off the aspiration tube.

According to a first aspect of the present invention there is provided apparatus for the provision of topical negative pressure therapy to a user, the apparatus comprising a device and a waste canister connected thereto, the waste canister being operably connected for receiving wound exudate to a wound dressing by an aspiration conduit which is releasably connected to the dressing, wherein the waste canister has a blank connector portion thereon for sealably receiving a disconnected dressing end of the aspiration conduit.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam, an inflatable bag or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

At the dressing end of the aspiration conduit there is a connector having one portion thereof permanently attached to the dressing end of the aspiration conduit and a second portion permanently attached to a (usually) relatively shorter portion of aspiration conduit which is part of and sealed to the dressing architecture which covers the wound. In some circumstances the user of the apparatus may wish to disconnect it from the dressing by means of disconnecting the releasable connector in the aspiration conduit adjacent the dressing. The reasons why a user may wish to disconnect the aspiration conduit and/or apparatus from the dressing may be many and varied but include, for example, the need to change the waste canister which may be full, the need to attend some other treatment in a hospital where the wearing of the apparatus may not be appropriate, the need to pass through security scanning apparatus when travelling. In whatever circumstances appertaining at the time there is a need to deal with the open dressing end of the aspiration conduit to prevent leakage therefrom. It has been standard practice to use a small clamp to squeeze off the open dressing end of the aspiration conduit but this has the disadvantages of being inconvenient, the need for a user to remember always to carry a suitable clamping device with them, the possibility of dropping or loosing a separate clamping device, the possibility of the disconnected end dragging on the ground or getting otherwise caught and being contaminated and an economic cost of an additional part of the apparatus. In some circumstances the same aspiration conduit may be re-connected to the dressing with the possibility of contamination and/or infection of the wound.

In the present invention a connector portion the same as that of the connector portion on the aspiration conduit portion sealed to the dressing is provided on the waste canister so that the free, disconnected dressing end of the aspiration conduit may be immediately connected thereto. The invention has the advantages that there can be no leakage from the disconnected dressing end of the aspiration conduit, it cannot become contaminated by contact with the ground or other surfaces, the connector portion on the waste canister can be provided at virtually no cost, there is no separate clamping device to loose or forget, the free, disconnected end of the aspiration conduit can be instantly reconnected to the dressing if desired and, the present invention provides a neat solution to conduit management.

The actual form of the connector in the aspiration conduit line is not of great importance, merely that the connector portion on the waste canister easily and sealably accepts the connector portion of the free, disconnected dressing end of the aspiration conduit.

There are many different methods of putting the present invention into effect. For example, the connector portion on the waste canister may aptly be an integral moulding on the canister or on a constituent part thereof, or a separate connector portion may be affixed to the canister such as by welding. Where the connector portion is an integral moulding on the canister it may be provided at virtually no extra cost by being incorporated in the tooling for canister production. The position of the connector portion on the waste canister is relatively unimportant save for fulfilling two major requirements of being convenient for a user to access and being economic to produce.

The connector portion on the waste canister will be blank ended in that there is no through path from the connector portion to the interior of the waste canister.

Whilst the connector portion is specified as being on the waste canister, it is pointed out that it could alternatively be on the device, for example. However, it is believed that the waste canister is the most appropriate site for the connector portion by removing the need to disconnect the aspiration conduit when disposing of a full canister.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 µm pore size, for example, in respect of sealing the canister against bacteria expulsion and 1 µm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

The carry case may be provided with an aperture covered by a displaceable flap to enable user access to a keypad for varying the therapy applied by the apparatus.

According to a second aspect of the present invention, there is provided a waste canister having a blank connector portion thereon, the waste canister being for topical negative pressure therapy apparatus according to the first aspect of the present invention.

BRIEF DESCRIPTION OF THE DRAWINGS

In order that the present invention may be more fully understood, examples will now be described by way of illustration only with reference to the accompanying drawings, of which.

DETAILED DESCRIPTION OF SOME EXEMPLIFYING EMBODIMENTS

Figure 1:
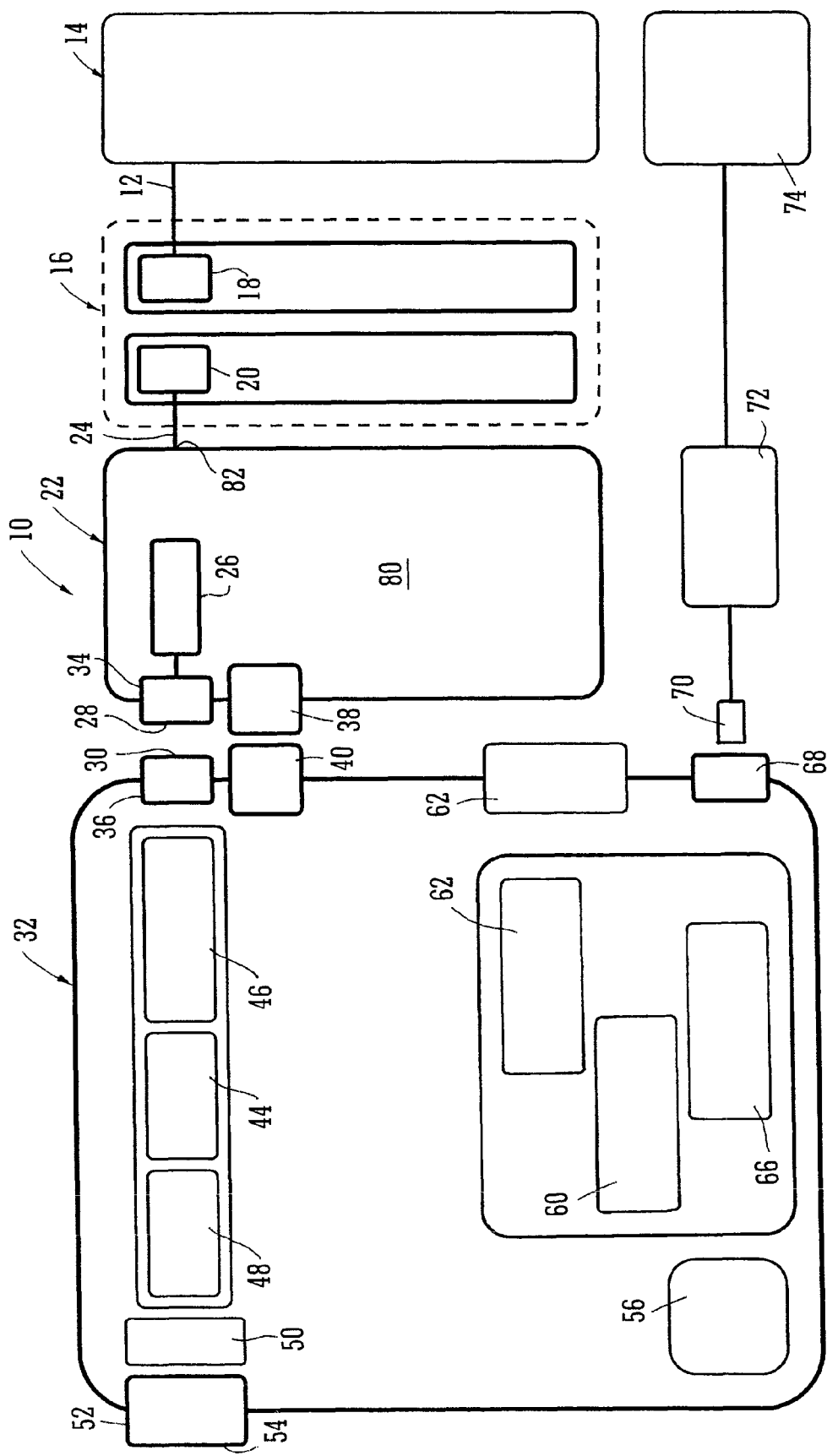
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 µm hydrophobic liquid filter and a 0.2 µm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
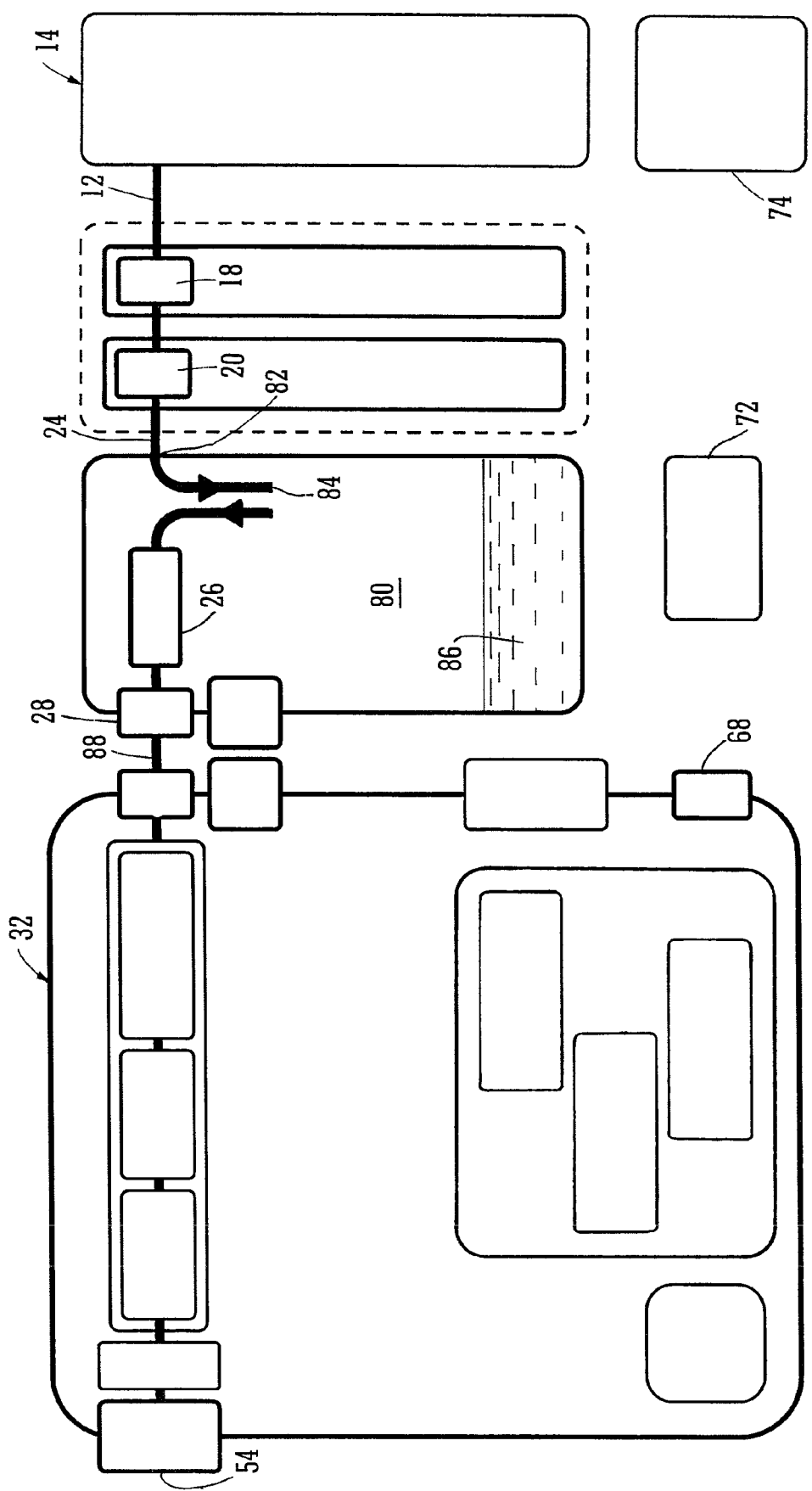
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
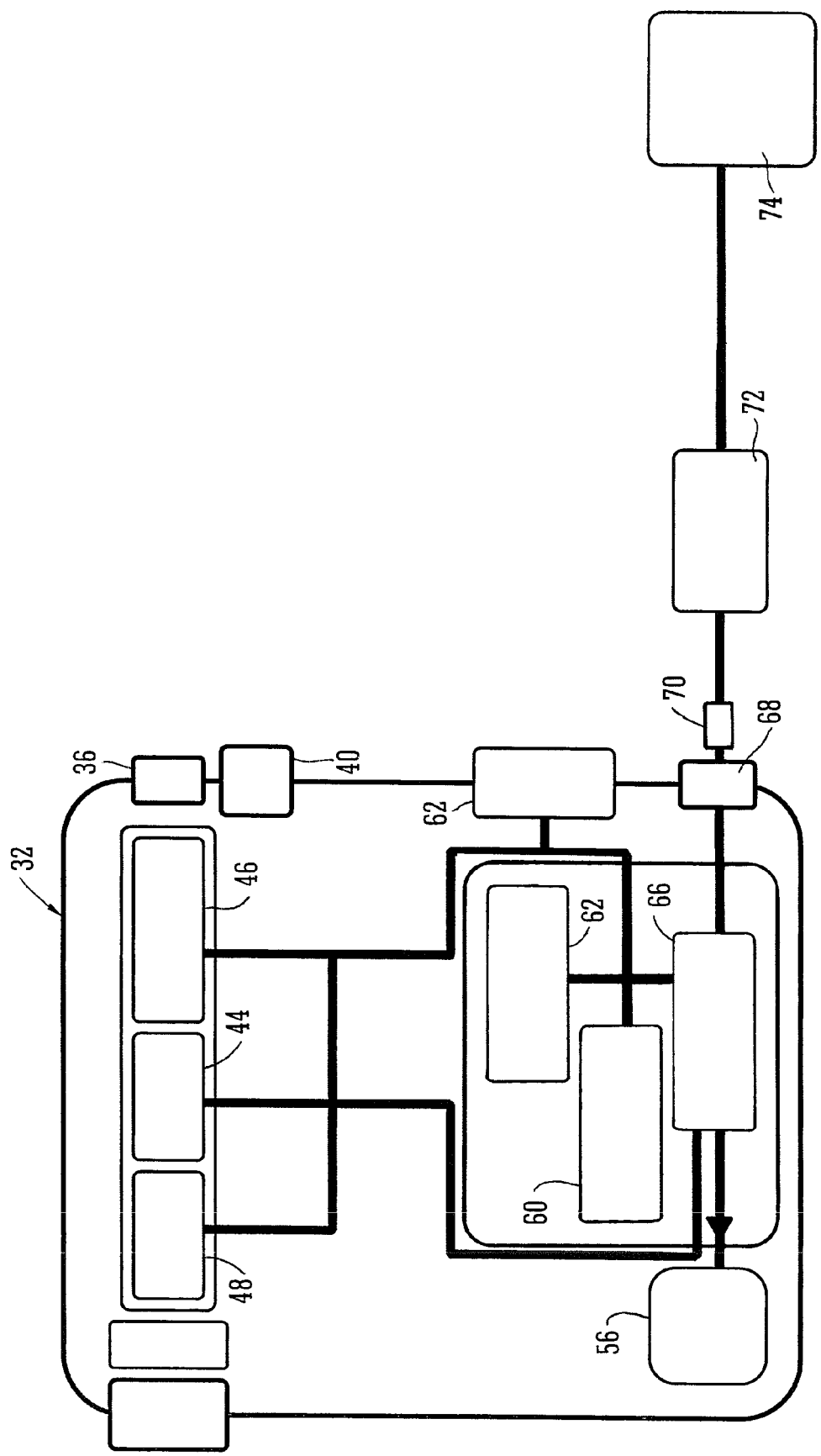
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
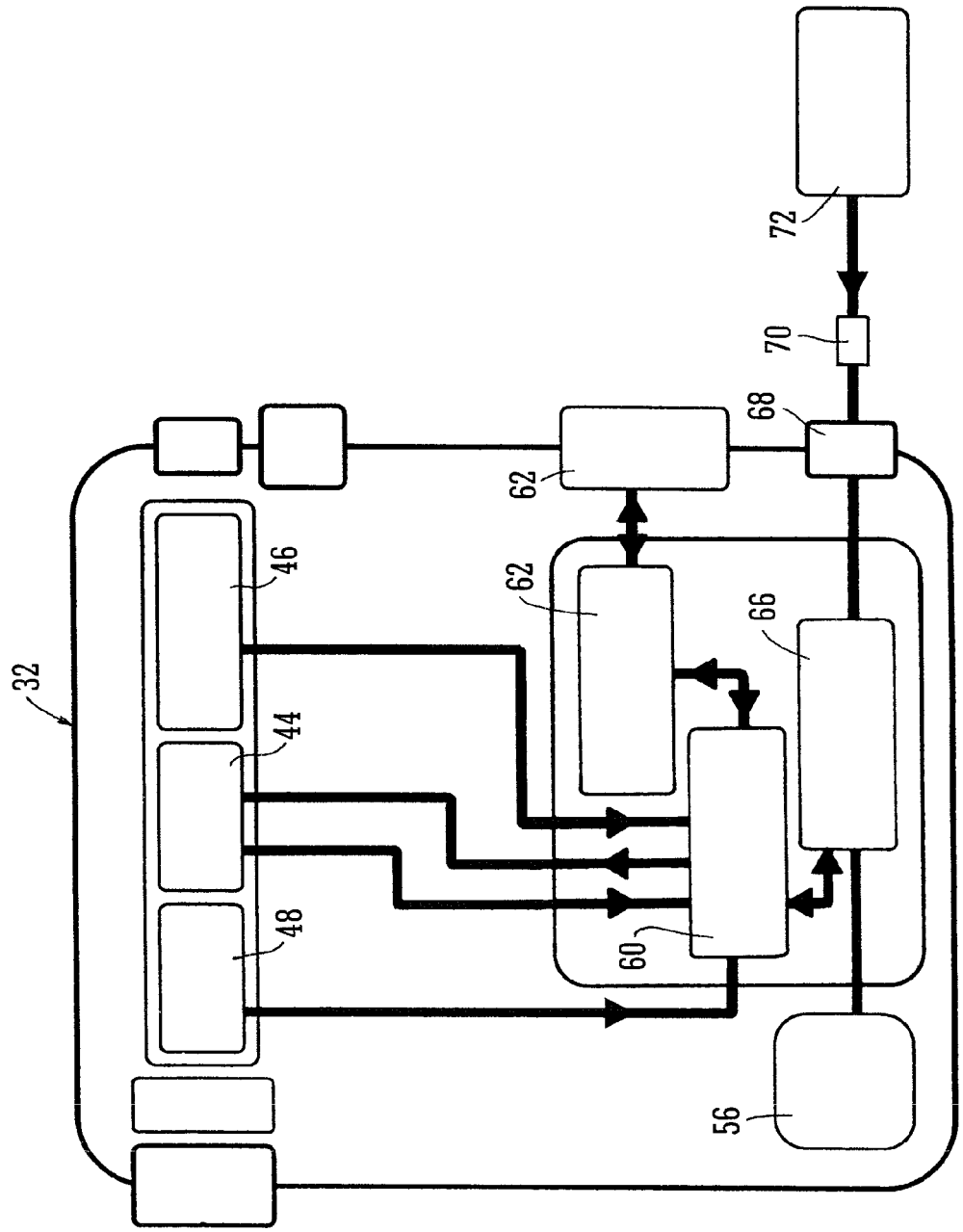
FIG. 4 shows a similar generalised schematic block diagram to FIG. 3 of the device unit and showing control system data paths for controlling the various functions and components of the apparatus.
Figure 5:
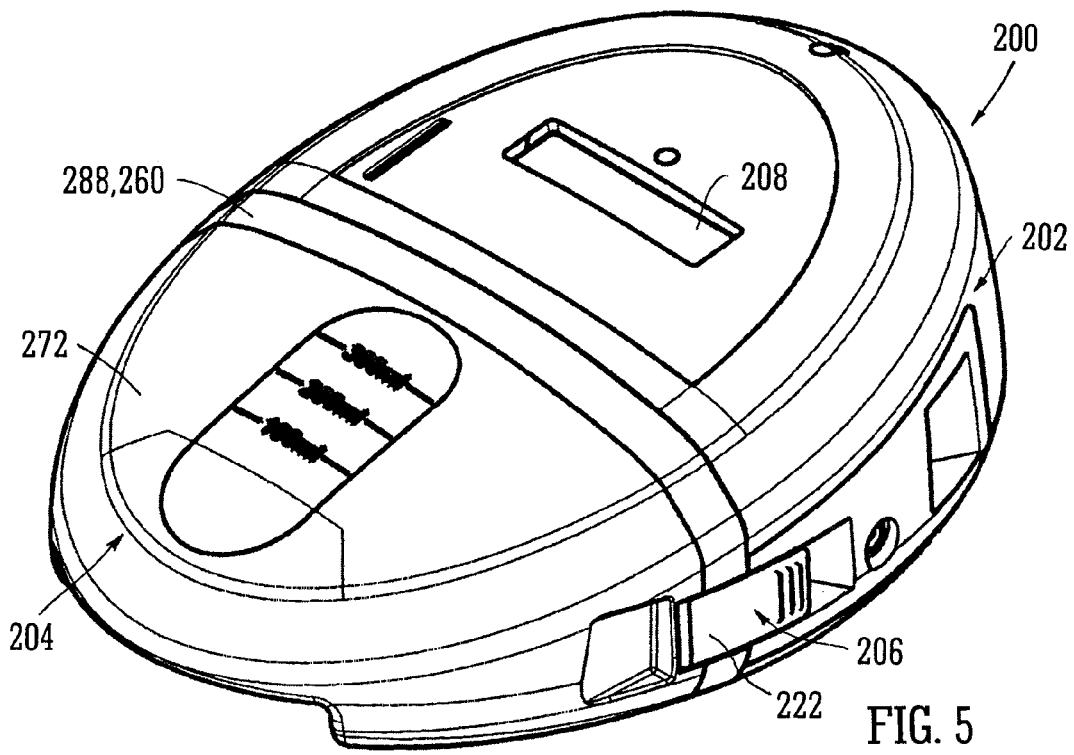
FIG. 5 shows a perspective view of an apparatus.
Figure 6:
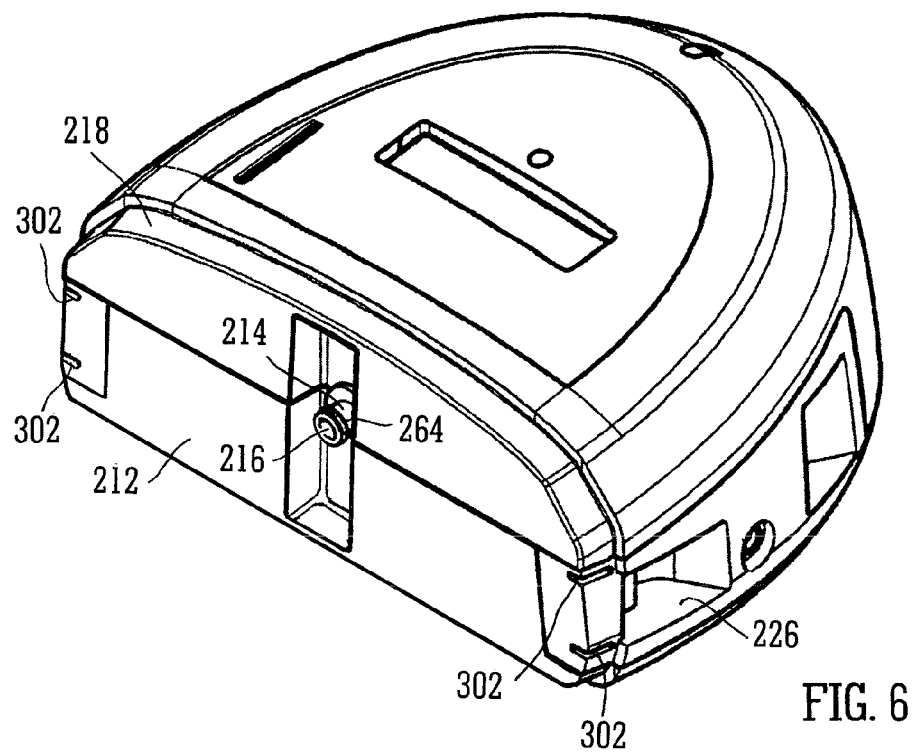
FIG. 6 shows a perspective view of an assembled device unit of the apparatus of FIG. 5.
Figure 7:
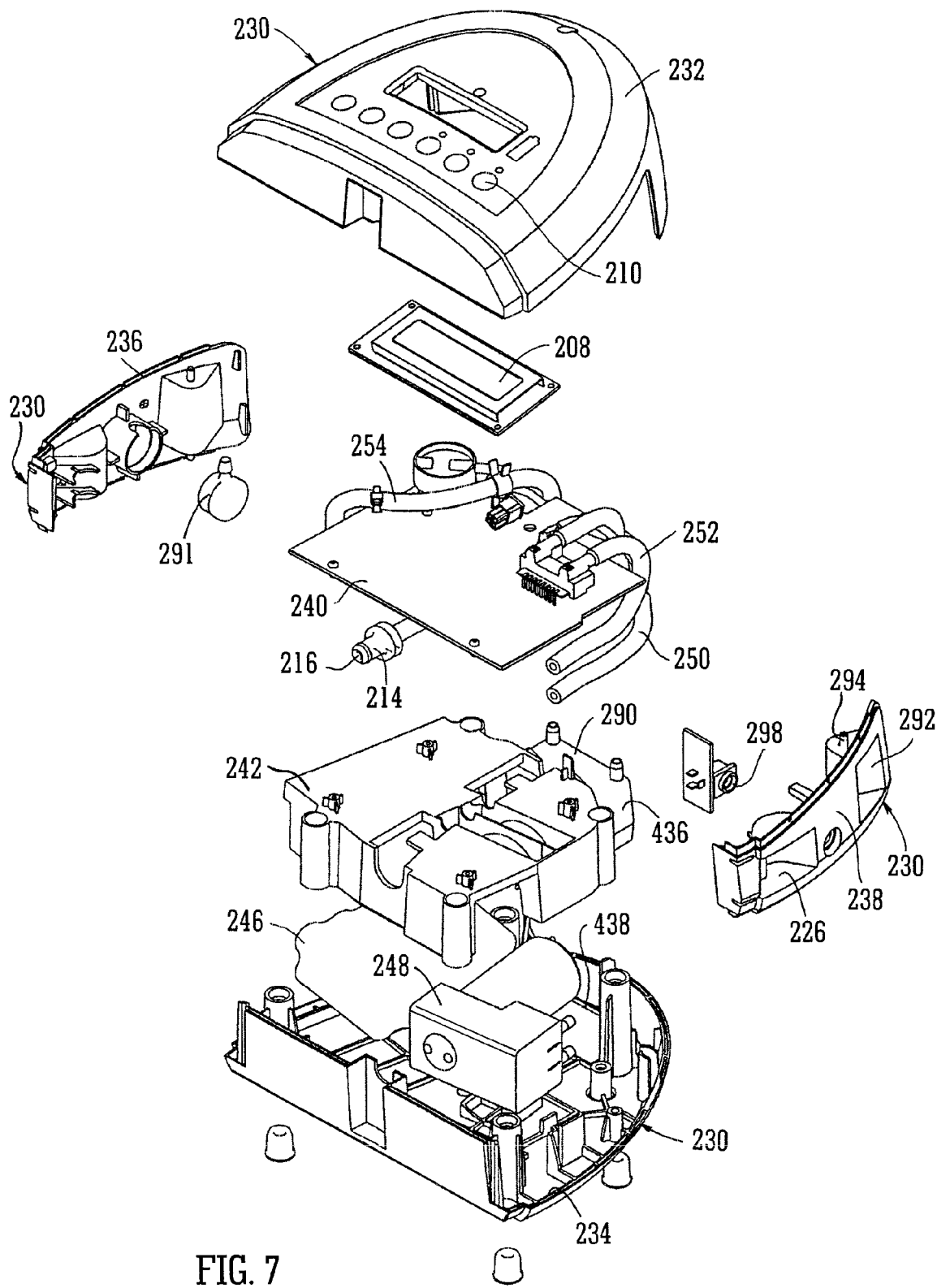
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
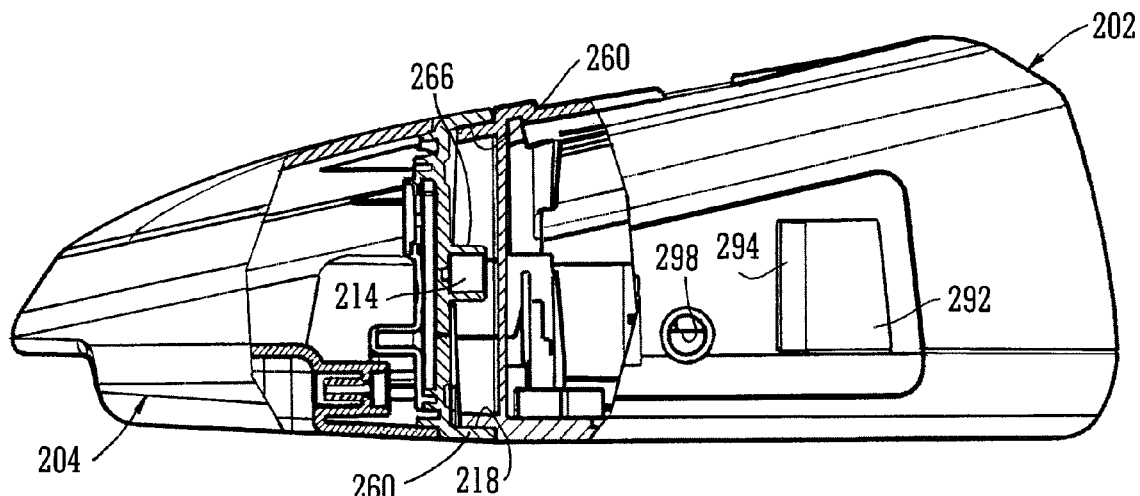
FIG. 8 shows a partially sectioned side elevation view through the interface between a waste canister and device unit of the apparatus.
Figure 9:
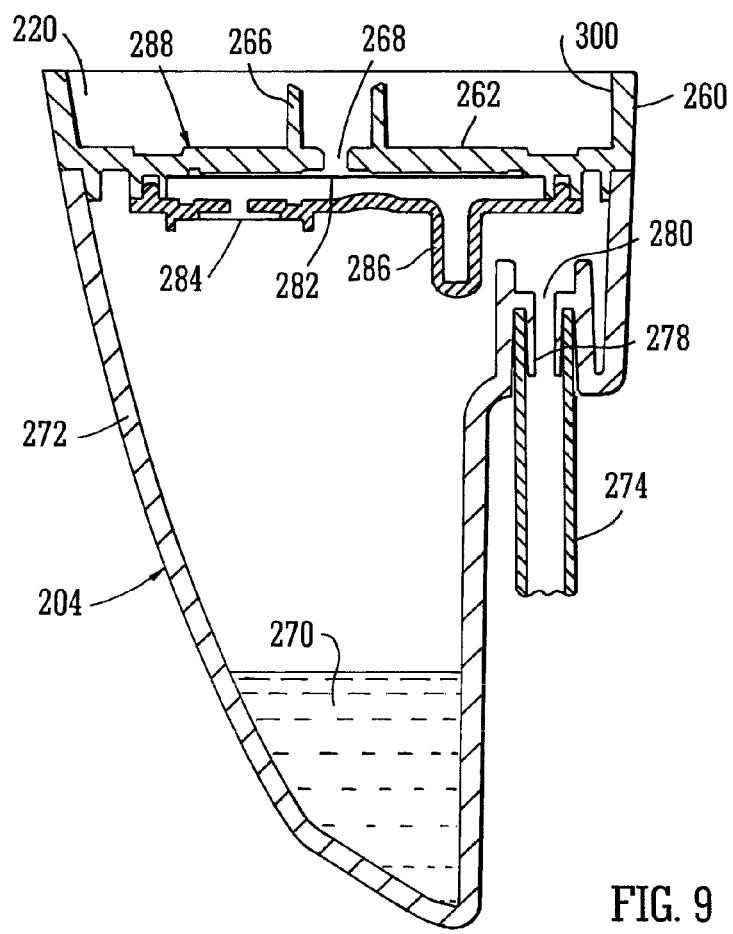
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. These views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 μm filter and 284 comprising a 1 μm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Referring now to FIGS. 10 to 13 and where the same features are denoted by the same reference numerals.

Figure 10:
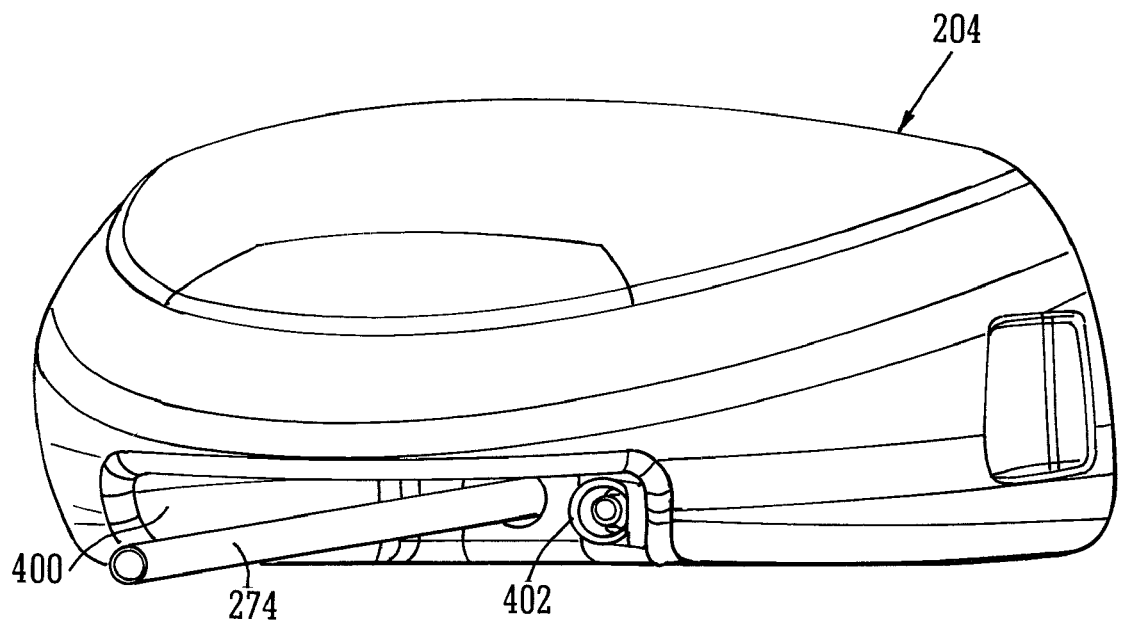
FIG. 10 shows a perspective view of a lower portion of a waste canister according to the present invention and having a blank connector portion.
Figure 11:
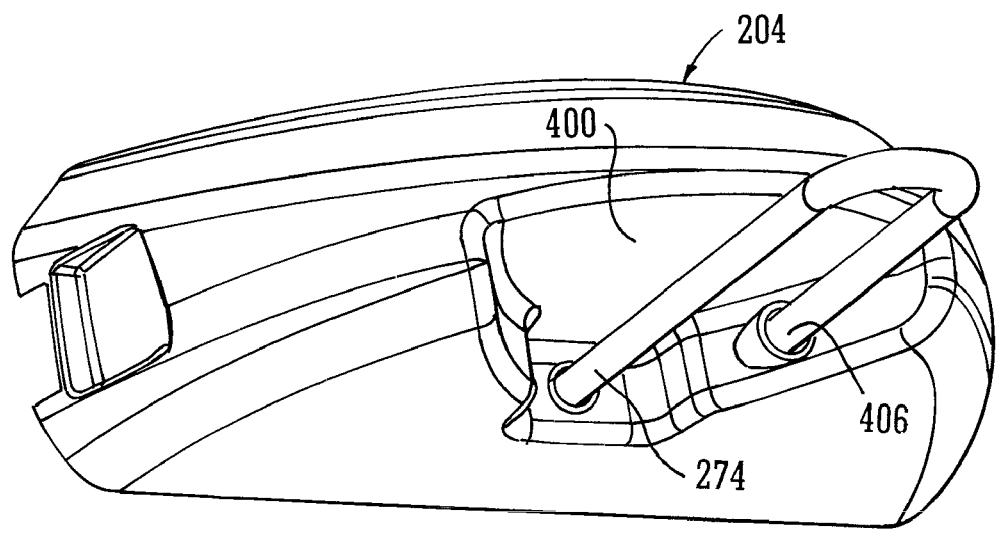
FIG. 11 shows the same view of the waste canister as FIG. 10 but showing a disconnected aspiration tube reconnected to the blank connector portion.
Figure 12:
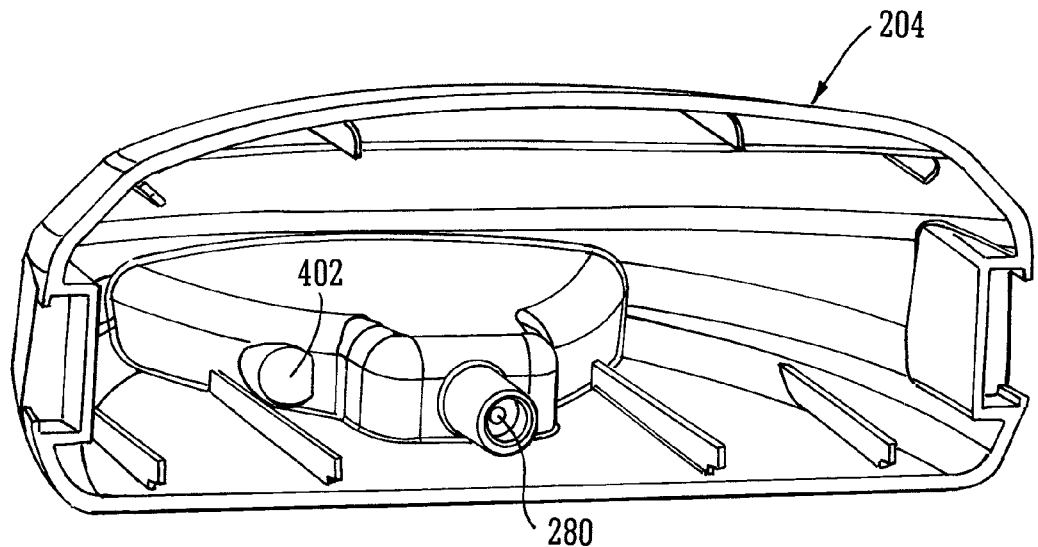
FIG. 12 shows an interior view of the waste canister of FIG. 10.
Figure 13A:
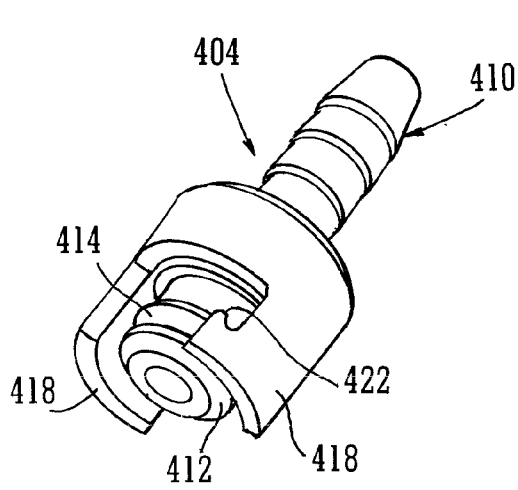
FIGS. 13A and 13B show perspective views one embodiment of male and female connector portions, respectively for connecting the aspiration conduit to a dressing aspiration conduit portion and also to the connector portion on the waste canister.
Figure 13B:
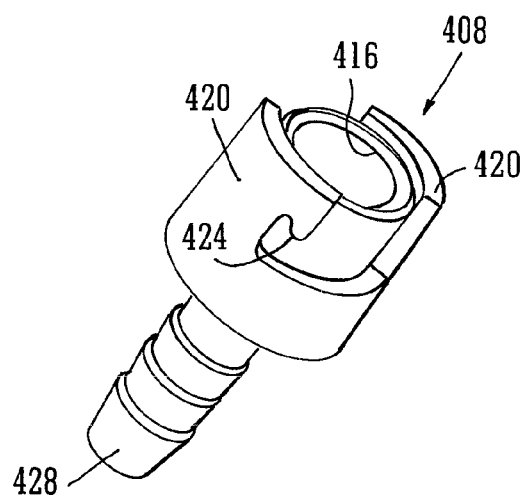

FIGS. 10 to 12 show a waste canister 204 substantially the same as that shown in section at FIG. 9 except for the fact that the canister top closure member 288 in FIG. 9 is omitted from FIG. 12 for the sake of clarity. FIGS. 10 and 11 both show the aspiration conduit 274 emerging from the entry port spigot 278 in a rear recess 400 moulded into the canister 204. Also moulded into the waste canister recess 400 is a blank female connector portion 402 to receive a male connector portion 404 affixed to the dressing end 406 of the aspiration conduit 274. The two connector portions 404, 408 (also denoted as 16, 18, 20 in FIG. 1) which connect the aspiration conduit 274 to the dressing 14 (see FIG. 1) via the relatively short conduit portion 12 (see FIG. 1) are shown in more detail in FIGS. 13A and 13B. The aspiration conduit 274 has at its dressing end a male connector portion 404 which has a barbed tubular spigot 410 for permanently fixing the connector portion to the dressing end of the aspiration conduit 274. The connector portion 404 has a male portion 412 having an "O" ring seal 414 therearound for sealably connecting with a co-operating female socket portion 416 in the female connector portion 408. The male and female connector portions 404, 408 are releasably held together by wall portions 418, 420 which have inter-engaging teeth 422, 424 members which engage and disengage by pushing the portions 404, 408 together and twisting relative to each other in the appropriate direction to engage or disengage the teeth members 422, 424. The female portion 408 also has a barbed tubular spigot 428 for permanently affixing to the relatively short conduit length 12 sealed to the dressing 14. As shown in FIG. 10, the waste canister has a blank female connector portion 402 integrally provided therewith and which in all physical respects corresponds to the female portion 408 except for the absence of the barbed tubular portion 428 and through hole. As may clearly be seen in FIG. 12 the site of the connector portion 402 is blanked off in the interior of the waste canister thus preventing passage of waste fluids either into or out of the waste canister.

When the aspiration conduit is disconnected from the dressing 14 by uncoupling the two connector portions 406, 408 as described above, the free, dressing end 406 and its connector portion 404 is immediately connected to the female connector portion 402 on the waste canister 204 ensuring sealing of the aspiration tube by the "O" ring seal 414 in the female socket portion of connector portion 402 (see FIG. 11). Thus the TNP apparatus may be removed by the wearer or a full canister discarded and a new canister installed as appropriate.

Whilst the connector portion 402 is specified above as being a female portion it is of course perfectly feasible to reverse the connector portion 404, 408 on the aspiration conduit and have a male portion 402 on the canister.

Figure 14A:
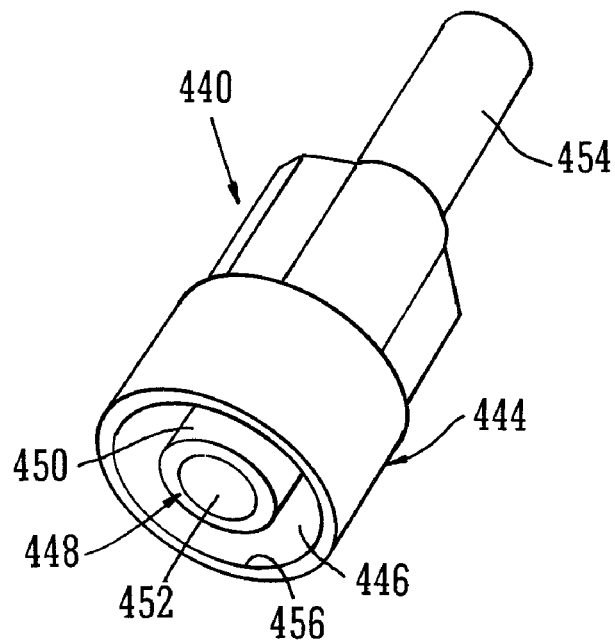
FIGS. 14A and 14B which show a second embodiment of male and female parts of a conduit connector which may be used in the present invention.
Figure 14B:
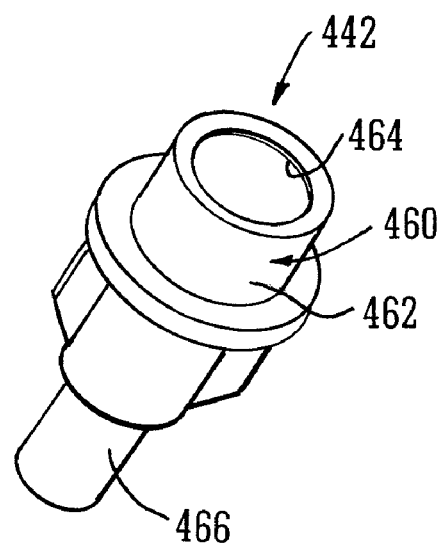

FIG. 14 shows a second embodiment of a connector for connecting the aspiration conduit to a dressing and which is similar to FIG. 13 described hereinabove. A male portion 440 is shown in FIG. 14A and a female portion 442 in FIG. 14B. The male portion 440 has an outer cylindrical body portion 444 surrounding an annulus 446 within which is a male spigot 448 having a tapered surface 450 on the outer surface thereof and bore 452 through the centre thereof. A tube connector 454 portion is also provided for connection to the aspiration conduit on the dressing (not shown). The female portion 442 has a cylindrical engaging portion 460, the outer surface 462 of which is sliding fit in an inner surface 456 of the cylindrical body portion of the male portion 440. The inner surface 464 of the cylindrical engaging portion 460 has a co-operating tapered form to co-operate with the tapered form of the spigot 448. The female portion 442 also has a conduit connection portion 466 for connection to an aspiration conduit. When the male and female portions 440, 442 are pushed together the two co-operating tapered surfaces 450, 464 form an interference fit.

In a modified version of the connector of FIG. 14, the inner surface 456 of the cylindrical wall portion 444 of the male portion 440 and the outer surface 462 of the female portion 442 may be provided with co-operating screw threaded portions (not shown) for a more secure connection.

As with the embodiment of FIG. 13, the waste canister is provided with the appropriate connector half to permit the aspiration conduit to be sealed off when disconnected from the dressing.

Whilst FIGS. 13 and 14 exemplify two particular embodiments of connectors there are of course many alternative designs that may be employed equally well but still fall within the scope of the present invention and is limited only by the claims appended hereto.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. An apparatus for the provision of topical negative pressure therapy to a wound on a user, the apparatus comprising:
    a device for providing a source of negative pressure to the wound;
    a waste canister connected thereto;
    an aspiration conduit connectable with the waste canister and the dressing and configured to communicate negative pressure from the device to the dressing; and
    a blank connector portion supported by the waste canister for sealably receiving a disconnected dressing end of the aspiration conduit, the blank connector being sealed to prevent passage of waste fluids into and out of the waste canister.

2. An apparatus according to claim 1, wherein the waste canister comprises at least one plastics material moulding.

3. An apparatus according to claim 2, wherein the blank connector portion is integrally moulded with the waste canister.

4. An apparatus according claim 2, wherein the blank connector portion is affixed to the waste canister.

5. An apparatus according to claim 1, wherein the blank connector portion is one of a male or a female connector portion and a connector portion on a dressing end of the aspiration conduit is the other of a male or a female connector portion.

6. An apparatus according to claim 5, wherein the blank connector portion and the connector portion on the dressing end of the aspiration conduit have mutual sealing means.

7. An apparatus according to claim 6, wherein the sealing means comprises an "O" ring seal.

8. An apparatus according to claim 6, wherein the sealing means comprises mutually tapered surfaces.

9. An apparatus according to claim 8, wherein the connector portions are provided with co-operating screw threaded portions.

10. An apparatus according to claim 1, the canister having integral filters in an outlet path thereof.

11. An apparatus according to claim 1, wherein the device for providing a source of negative pressure to the wound comprises a control system configured to trigger alarm means when an abnormal condition in the apparatus is encountered.

12. An apparatus according to claim 1, wherein the blank connector is configured such that there is no through path from the connector portion to the interior of the waste canister.

13. A method of using the waste canister of claim 1, comprising:
    disconnecting the dressing end of the aspiration conduit from the dressing; and
    connecting the dressing end of the aspiration conduit to the blank connector portion supported by the waste canister to secure the dressing end of the aspiration conduit and to prevent any substances within the aspiration conduit from flowing out of the dressing end of the aspiration conduit.

14. An apparatus for the provision of topical negative pressure therapy to a wound on a user, the apparatus comprising:

a negative pressure device for providing a source of negative pressure to the wound;

a waste canister connected thereto;

an aspiration conduit connectable with the waste canister and the dressing and configured to communicate negative pressure from the device to the dressing; and a blank connector portion supported by the negative pressure device for sealably receiving a disconnected dressing end of the aspiration conduit, the blank connector being sealed to prevent passage of waste fluids into and out of the disconnected dressing end of the aspiration conduit.

15. An apparatus according to claim 14, wherein the blank connector portion is integrally moulded with the negative pressure device.

16. An apparatus according claim 14, wherein the blank connector portion is affixed to the negative pressure device.

17. An apparatus according to claim 14, wherein the blank connector portion is one of a male or a female connector portion and a connector portion on a dressing end of the aspiration conduit is the other of a male or a female connector portion.

18. An apparatus according to claim 17, wherein the blank connector portion and the connector portion on the dressing end of the aspiration conduit have at least one of an "O" ring seal, mutually tapered surfaces, and co-operating screw threaded portions.

19. A method of using the waste canister of claim 14, comprising:

disconnecting the dressing end of the aspiration conduit from the dressing; and connecting the dressing end of the aspiration conduit to the blank connector portion supported by the negative pressure device to secure the dressing end of the aspiration conduit and to prevent any substances within the aspiration conduit from flowing out of the disconnected dressing end of the aspiration conduit.

* * * * *

UNITED STATES PATENT AND TRADEMARK OFFICE
CERTIFICATE OF CORRECTION

PATENT NO. : 8,333,744 B2
APPLICATION NO. : 12/672192
DATED : December 18, 2012
INVENTOR(S) : Hartwell et al.

Page 1 of 1

It is certified that error appears in the above-identified patent and that said Letters Patent is hereby corrected as shown below:

In the Specification

Column 2, line 21, change "form" to --from--.

In the Claims

Column 12, line 29, in Claim 4, after "according" insert --to--.

Column 13, line 17, in Claim 16, after "according" insert --to--.

Signed and Sealed this
Thirty-first Day of December, 2013

Margaret A. Focarino
*Commissioner for Patents of the United States Patent and Trademark Office*